United States Patent
Bahmanyar et al.

(10) Patent No.: US 11,800,987 B2
(45) Date of Patent: Oct. 31, 2023

(54) IMPLANTABLE INTRAVASCULAR SENSING DEVICE

(71) Applicant: IP2IPO INNOVATIONS LIMITED, London (GB)

(72) Inventors: Mohammad Reza Bahmanyar, London (GB); Christopher Neil McLeod, London (GB)

(73) Assignee: IP2IPO INNOVATIONS LIMITED, London (GB)

( * ) Notice: Subject to any disclaimer, the term of this patent is extended or adjusted under 35 U.S.C. 154(b) by 1000 days.

(21) Appl. No.: 16/334,822

(22) PCT Filed: Sep. 20, 2017

(86) PCT No.: PCT/GB2017/052804
§ 371 (c)(1),
(2) Date: Mar. 20, 2019

(87) PCT Pub. No.: WO2018/055369
PCT Pub. Date: Mar. 29, 2018

(65) Prior Publication Data
US 2019/0343403 A1   Nov. 14, 2019

(30) Foreign Application Priority Data
Sep. 21, 2016   (GB) ..................... 1616091

(51) Int. Cl.
*A61B 5/0215*   (2006.01)
*A61B 5/00*   (2006.01)
(Continued)

(52) U.S. Cl.
CPC .......... *A61B 5/0215* (2013.01); *A61B 5/0031* (2013.01); *A61B 5/686* (2013.01);
(Continued)

(58) Field of Classification Search
CPC ....... A61B 5/0215; A61B 5/00; A61B 5/0031; A61B 5/6882; A61B 5/686;
(Continued)

(56) References Cited

U.S. PATENT DOCUMENTS

| 2006/0001123 A1* | 1/2006 | Heck | ..................... B81C 1/0023 |
| | | | 257/528 |
| 2007/0220986 A1* | 9/2007 | Smith | ..................... G01L 9/008 |
| | | | 73/727 |

(Continued)

FOREIGN PATENT DOCUMENTS

WO   20180055369 A1   3/2018

OTHER PUBLICATIONS

Office Action dated May 20, 2020 for Great Britian Patent Appl. No. GB1715276.0, 2 Pages.

(Continued)

*Primary Examiner* — Eric J Messersmith
(74) *Attorney, Agent, or Firm* — Maine Cernota & Curran (57) ABSTRACT

An implantable intravascular device for deployment inside a human or animal, the apparatus comprising a body of crystalline material and a membrane of crystalline material fixed to the body by a hermetic bond an assembly of components carried on said crystalline material and arranged for responding to electrical signals wherein the body and the membrane at least partially encapsulate the assembly.

11 Claims, 6 Drawing Sheets

(51) Int. Cl.
*B23K 35/30* (2006.01)
*C22C 5/02* (2006.01)
*G01L 13/00* (2006.01)
*H01Q 1/27* (2006.01)

(52) U.S. Cl.
CPC ............ *B23K 35/3013* (2013.01); *C22C 5/02* (2013.01); *G01L 13/00* (2013.01); *H01Q 1/273* (2013.01); *A61B 5/6876* (2013.01)

(58) Field of Classification Search
CPC .... A61B 2562/0247; A61B 2560/0238; A61B 2562/12; A61B 5/6876; B23K 35/30; B23K 35/3013; C22C 5/02; G01L 13/00; H01Q 1/27; H01Q 1/273
See application file for complete search history.

(56) References Cited

U.S. PATENT DOCUMENTS

| | | | | |
|---|---|---|---|---|
| 2007/0267708 | A1* | 11/2007 | Courcimault | ....... B81C 1/00301 |
| | | | | 257/414 |
| 2011/0036173 | A1 | 2/2011 | Chommeloux et al. | |
| 2015/0342470 | A1* | 12/2015 | Cros | .................... A61B 5/6882 |
| | | | | 29/831 |
| 2016/0058324 | A1 | 3/2016 | Cao | |
| 2016/0324443 | A1* | 11/2016 | Rowland | ................. A61B 5/01 |

OTHER PUBLICATIONS

PCT Search Report & Written Opinion for Appl No. PCT/GB2017/052804 dated Dec. 21, 2017, 19 pages.

\* cited by examiner

IMPLANTABLE INTRAVASCULAR SENSING DEVICE

RELATED APPLICATIONS

This application is a national phase application filed under 35 USC § 371 of PCT Application No. PCT/GB2017/052804 with an International filing date of Sep. 20, 2017 which claims priority of GB Patent Application 1616091.3 filed Sep. 21, 2016. Each of these applications is herein incorporated by reference in their entirety for all purposes. This application is related to PCT Application No. PCT/GB2017/052801 with an International filing date of Sep. 20, 2017 which claims priority of GB Patent Application 1616096.2 filed Sep. 21, 2016; PCT Application No. PCT/GB2017/052802 with an International filing date of Sep. 20, 2017 which claims priority of GB Patent Application 1616090.5 filed Sep. 21, 2016; PCT Application No. PCT/GB2017/052834 with an International filing date of Sep. 21, 2017 which claims priority of GB Patent Application 1616092.1 filed Sep. 21, 2016; and PCT Application No. PCT/GB2017/053313 with an International filing date of Nov. 2, 2017 which claims priority of GB Patent Application 1618508.4 filed Nov. 2, 2016; each of these applications is herein incorporated by reference in its entirety for all purposes.

FIELD

This application relates to implantable devices for implanting into the human or animal body. Such devices may generally be implanted in any part of the body and include, for example, implantable intravascular devices for deployment inside the vasculature of the human or animal body.

BACKGROUND

Medical technology is progressing rapidly, and in particular there has been an increase in the range of implantable devices available for providing a variety of measurements of the vital signs of a patient to a physician. Internal measurements may be beneficial, since they are able to measure a true, local value. Implantable devices are preferred for taking internal measurements, as repeatedly inserting and removing devices can be detrimental to a patient's health. Where there is a need for long-term monitoring of patients the repeated use of invasive measurements increases the risk of injury and can ultimately lead to the physician deciding that such a procedure is too risky to undertake.

Once implanted, such sensors can provide information over a long period without further risk each time they are used. Communication with the implant can be achieved through inductive coupling or through a radio-frequency link from a transmitter/receiver located outside the patient's body.

WO2005058166 discloses an implantable, or wearable sensor for monitoring parameters, such as pressure, temperature, viscosity, or flow rate within a human or animal body. This document discloses a method of monitoring a parameter of a human or animal body wherein a surface acoustic wave device is implanted therein or attached thereto, wherein the device comprises a pair of interdigitated transducers spaced apart over the surface of a piezoelectric substrate, that is exposed to the parameter, wherein an antenna is connected to one of the interdigitated transducers, wherein a radio-frequency signal is supplied externally of the body to the antenna, is transmitted over the substrate surface to the other of the transducers, reflected therefrom back to the said one of the transducers and transmitted from the antenna thereof to a receiver, whereby comparison of the supplied and received signal provides a measurement of the parameter.

In many applications, it can be desirable to provide a reference measurement in addition to the measurement being taken, for example to compare the measured data to a known reference, for ease of calibration. When implanted, however, the environment in which the device finds itself is prone to change, and it can be difficult to provide a reference which is not affected by the external environment.

Also, since such devices must necessarily be small, so as not to adversely affect the patient's health, difficulties may be encountered in securing the device to other devices, for example anchors or electrical antennas.

SUMMARY

Aspects and embodiments of the present disclosure aim to address at least some of these drawbacks. Aspects and embodiments are set out in the appended claims. These and other aspects and embodiments are also described herein.

Described herein is an implantable intravascular device for deployment inside a human or animal (body), the apparatus comprising: a body of crystalline material and a membrane of crystalline material fixed to the body by a hermetic bond; an assembly of components carried on said crystalline material and arranged for responding to electrical signals; wherein the body and the membrane at least partially encapsulate the assembly.

The encapsulation of at least part of the assembly using a hermetic seal allows at least part of the assembly to be provided with a reference environment. For example, pressure, humidity, chemical makeup etc. may be fixed by providing the environment inside the hermetic seal, within which part of the assembly is encapsulated. In this example, the environment inside the hermetic seal may be used as a reference environment, as it remains unaffected by the external environment in which the device is located. This environment may be useful for providing a reference environment for calibrating the device.

Optionally, the hermetic bond comprises a metal interlayer between the membrane and the body, for example wherein the metal interlayer forms a diffusion bond such as a thermo-compression bond. Moreover, the hermetic bond may comprise a eutectic bond. Such bonds provide good isolation from the environment, and are easy to make without damaging the device.

The eutectic bond may comprise gold, for example gold comprising a dopant material which lowers the bonding temperature such as indium or tin. Such compositions allow the bond to be formed at low temperatures, thereby reducing thermal strains on the device during the manufacture.

Optionally, the apparatus comprises a cap secured to the body, and at least one channel between the cap and the body. The cap arrangement allows external components to be easily connected to the device.

The cap and the body may be made from the same crystalline material. This may reduce stresses generated by differential thermal expansion during the sealing process, which requires the temperature of the device to be raised.

Optionally, the at least one channel is provided by at least one trench disposed in at least one of the cap and the body and at least partially covered by the respective other one of the cap and the body. Trenches are easy to form in crystalline materials thus making the production of such devices cheaper and more efficient.

Moreover, the at least one channel may comprise an open end to enable an elongate member to be partially disposed in and extend from the at least one channel, for example the at least one channel comprises a connection channel for securing an antenna to the apparatus. Antennas provide a convenient means for communicating with the device, even when it is implanted into a human or animal body, and is not in direct line of sight. Antennas are often elongate, making a channel a useful shape for attaching an antenna to the device.

The at least one channel may further comprise a fixture channel for fixing the apparatus to a strut of an anchor for anchoring (i.e. supporting) the apparatus to a structure inside the human or animal body. For example, the at least one channel may comprise a fixture channel for fixing the apparatus to a strut of an intravascular anchor for supporting the apparatus in a vascular lumen. It can be useful to ensure that the device remains in a fixed location inside the human or animal body, for example to ensure that a series of consecutive measurements are directly comparable to one another, as they are taken at the same location. Anchors often comprise wires or other elongate parts, making a channel a useful shape for attaching the device to such anchors.

The trench may be disposed in a major surface of the body and/or the cap. Forming a trench on a major surface allows for longer trenches, thereby improving the ability of the trench to grip elongate members, e.g. of anchors or antennas.

Also described herein is an implantable device for deployment inside a human or animal body, comprising: a body of crystalline material carrying an assembly of components arranged for responding to electrical signals; a cap secured to the body; and a connection channel, between the cap and the body, for securing an antenna to the apparatus for communicating electrical signals to and from the assembly (of components). An antenna provides convenient means for communicating with such a device while the device is embedded within a human or animal body. The use of a cap with a channel to achieve this provides a convenient way of attaching the antenna to the device.

The cap and the body may be made from the same crystalline material. For example, the cap and the body may be made essentially of the same material. As a further example, both the cap and the body may each consist entirely of the same material. This reduces thermal stressing of the device due to differential thermal expansion.

The device may also comprise a fixture channel, between the cap and the body, for fixing the apparatus to a strut disposed in the fixture channel. The use of a cap with a channel to achieve this provides a convenient way of attaching the device to external fixtures, e.g. anchors.

Also disclosed herein is an implantable device for deployment inside a human or animal body, comprising: a body of crystalline material carrying an assembly of components arranged for responding to electrical signals; a cap secured to the body; and a fixture channel, between the cap and the body, for fixing the apparatus to a strut disposed in the channel. Implantable devices may be connected to other devices inside the human or animal body. Such devices may include struts to which the implantable device may be attached. The use of a cap with a channel provides a convenient way of attaching the implantable device to other devices, by positioning such a strut in the channel of the implantable device. Again, the cap may be of the same crystalline material as the body.

The strut may comprise a strut of an intravascular anchor for supporting the apparatus in a vascular lumen. It is often desirable to ensure that the implantable device does not move relative to the human or animal body, so an anchor is used.

Optionally the device may comprise a membrane of crystalline material fixed to the body by a hermetic bond. The membrane and hermetic bond may provide protection from the external environment to parts of the device.

Moreover, the body may comprise a cavity and the hermetic bond seals the cavity to provide a sealed enclosure at a reference pressure. The sealed cavity prevents gas escaping from the cavity into the human or animal body optionally the assembly is arranged to provide a pressure sensor for sensing intravascular pressure as compared to said reference pressure. Reference pressures are useful in calibrating the device.

The body discussed above may comprise at least one via in the crystalline body for connection with the assembly. The via may allow communication between components on a first side of the device and components on a second, opposing side of the device. Moreover, the via may be arranged for communicating electrical signals between the connection channel and the assembly. Transferring electrical signals through the body allows components located on different parts of the assembly to communicate with one another.

The via may terminate in the connection channel. For example, the via provides a path for the conduction of electrical signals into the sealed enclosure. This allows communication between the antenna and other components.

The via may be at least partially filled with a first conductor and closed by a second conductor more ductile than the first conductor, for example wherein the second conductor comprises gold. The use of a more ductile material to close the via means that if the shape of the via distorts, e.g. due to thermal expansion, the seal may remain in place.

The via may be closed by a hermetic bond. This may ensure that any sealed cavities in the body remain hermetically sealed.

The membrane may be coupled to a first side of the body and the cap is disposed on a second side, opposite to the first side. This arrangement may be easier and cheaper to produce.

The crystalline material may comprise a piezoelectric material. Piezoelectric materials may form part of a sensing apparatus, in conjunction with the assembly of components, the crystalline material may comprise quartz, for example.

In addition, the assembly of components optionally comprises at least one interdigitated transducer, IDT. Moreover, the crystalline material may provide the substrate of the at least one IDT. IDTs may make use of piezoelectric substrates to generate surface acoustic waves as part of a measurement.

At least one of the membrane and the body may be arranged so that the crystalline material at least partially encapsulates the at least one IDT. This isolates the IDT from the external environment, for example for protection, or to allow it to perform a reference measurement, unaffected by the external environment.

The at least one IDT may comprise a first IDT disposed on the membrane to sense intravascular pressure based on deflection of the membrane. Optionally, the at least one IDT comprises a second IDT disposed on a region of the crystalline material arranged to be deflected less by changes in intravascular pressure than the region which carries the first IDT. Moreover, the second IDT may be disposed on the membrane.

Optionally, the first IDT and the second IDT are both aligned with the same crystal plane orientation of the crystalline material. This may simplify the comparison of the outputs of the two IDTs.

The crystalline material may be bonded using a room temperature bond, for example, the bond may comprise a surface treatment of the crystalline material such as Fast Atomic Bombardment. This reduces the thermal strain on the device during the bonding process.

The body of crystalline material may be bonded to the cap by an elevated temperature bond, for example a diffusion bond, for example a thereto-compression bond. The bond may further comprise a eutectic bond. Moreover, the eutectic bond may comprise gold, for example gold comprising a dopant material which lowers the bonding temperature such as indium or tin. The dopant may comprise at least 15% by mass of the bond, for example at least 20%, for example at least 25%. Preferably, the dopant is 20% of the bond of the dopant is Sn (e.g. Au—Sn), or preferably 27% of the bond when the dopant is In (e.g. Au—Sn). Such bonds show good strength while allowing for a low temperature bonding process, which reduces thermal strain on the device while bonding occurs.

The apparatus described herein may further comprise at least one of: an antenna having a stem for fixing in a connection channel of the apparatus; and an anchor for deploying the device in a human or animal body, wherein the anchor comprises at least one strut for fixing in a fixture channel of the apparatus. This allows the construction of an apparatus which may communicate with external apparatus via an antenna; and/or which may be fixed in place in the body, for example a vascular lumen, thereby reducing the risk of losing the device, and ensuring that measurements may be compared with one another.

BRIEF DESCRIPTION OF THE DRAWINGS

Aspects and embodiments will now be described, by way of example only, with reference to the accompanying drawings, in which.

DETAILED DESCRIPTION

Figure 1:
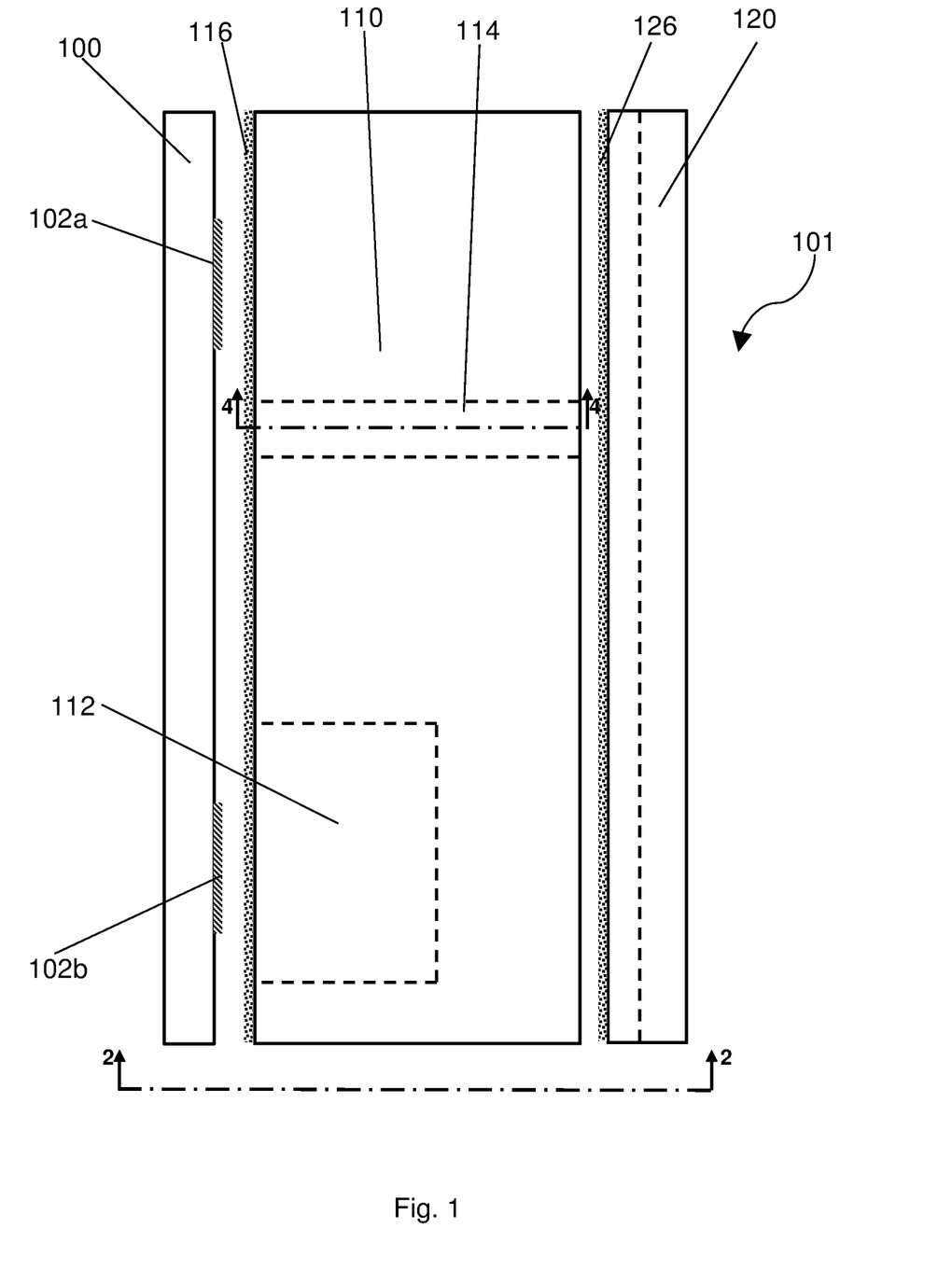
FIG. 1 shows a side view of an implantable device.
Figure 2:
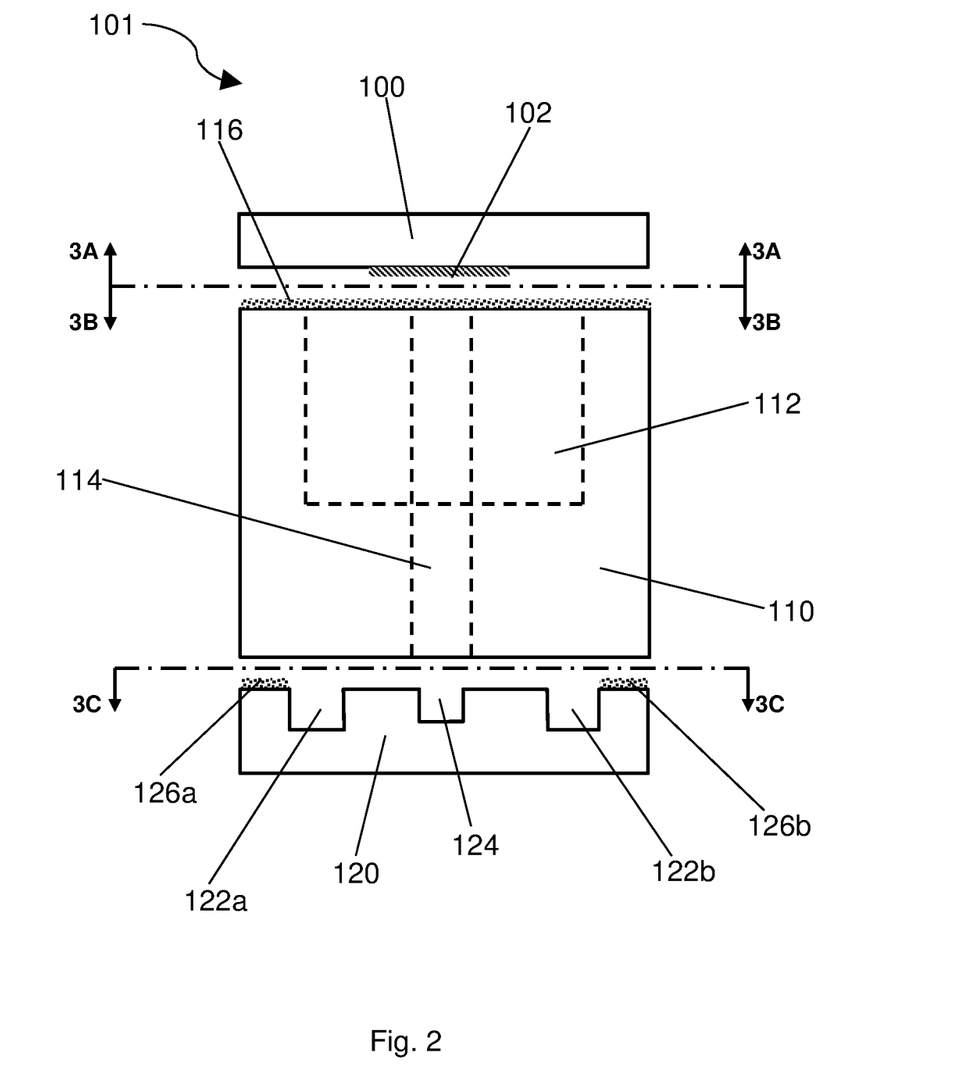
FIG. 2 shows a front view of an implantable device, showing the view in the direction of the arrows from section line 2-2 in FIG. 1.
Figure 3A:
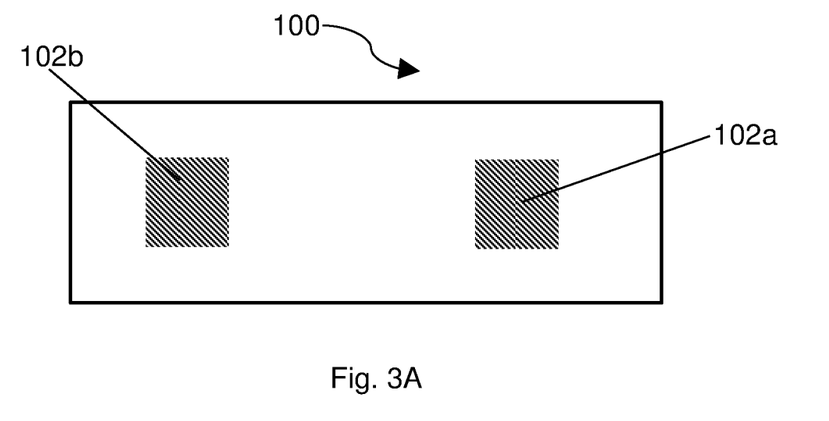
FIG. 3A shows a bottom view of part of an implantable device, showing the view in the direction of the arrows from section line 3A-3A in FIG. 2.
Figure 3B:
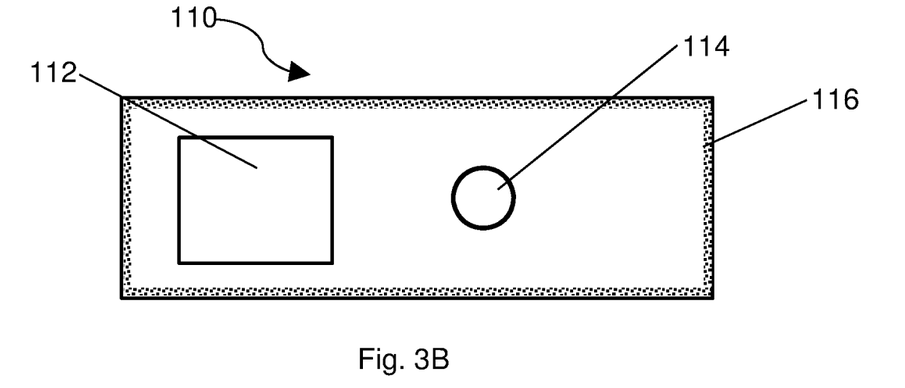
FIG. 3B shows a top view of part of an implantable device, showing the view n the direction of the arrows from section line 3B-3B in FIG. 2.
Figure 3C:
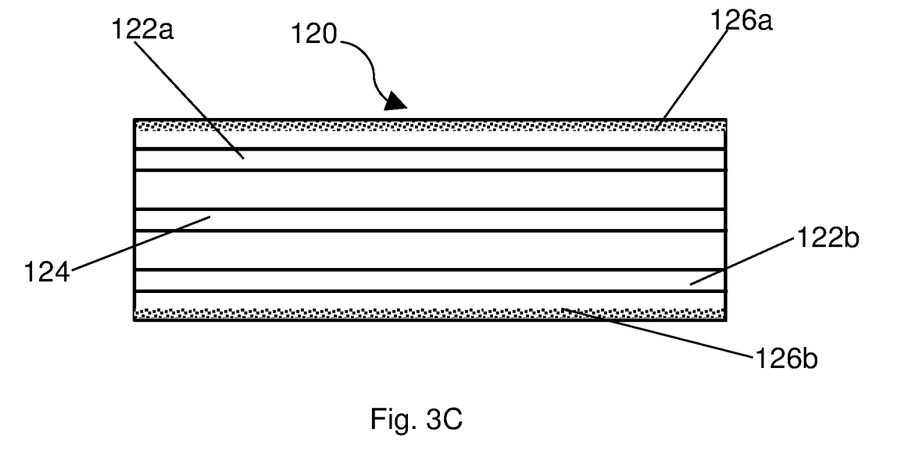
FIG. 3C shows a top view of part of an implantable device, showing the view in the direction of the arrows from section line 3C-3C in FIG. 2.

FIGS. 1, 2, 3A, 3B and 3C illustrate various views of the components which make up an implantable device 101, suitable for implanting into a human or animal body. In each figure the same numbers refer to the same parts, and the following description of the device refers in general to this set of Figures. In general, FIG. 1 shows a side view of the components, FIG. 2 shows an end view of the components, and FIGS. 3A to 3C show plan views of each of the components. Dot-dashed lines in these Figures illustrate sectional lines, and are numbered with Figure numbers which show that view (in the direction of the arrows). Therefore, for example, the dot-dashed line labelled 2-2 in FIG. 1 illustrates the plane and direction from which the device is shown in FIG. 2.

As shown, the implantable device 101 comprises a membrane 100 upon which an assembly of components 102 is carried. In this example, the assembly of components comprises two components 102a and 102b carried on the membrane.

The device 101 also comprises a body 110, arranged to be joined to the membrane by a hermetic bond 116 between the upper surface of the body 110 and the lower surface of the membrane 100. The body includes a cavity 112 extending from its upper surface towards the lower surface of the body, but not penetrating entirely through the body 110. When assembled, the hermetic seal 116 ensures that the cavity 112 is isolated from the environment exterior to the implantable device 101.

The body 110 of the device is also provided with a via 114, which in this example is a cylindrical bore connecting the top and bottom surfaces of the body 110 of the device.

Located below the body 110 is a cap 120. The cap has a series of channels in it. Two channels 122a, 122b are fixture channels, while a third channel 124 is a connection channel. The cap also includes joints 126a and 126b which join the body 110 to the cap 120. Each channel 122, 124 extends entirely across a major surface of the cap, in other words across one of the faces of the cap which has the largest surface area. The function of the cap and the channels will be described in more detail below, with reference to FIGS. 5 and 6.

In each of FIGS. 1, 2, 3A, 3B and 3C, the membrane 100, body 110 and cap 120 are shown separate from one another for clarity. However, when assembled, the membrane 100 is attached to the upper surface of the body 110 by the hermetic seal 116. The hermetic seal 116 also ensures that the cavity 112 is isolated from the external environment. For example, the cavity 112 may contain gas at a preselected pressure (that is, selected during manufacture), and the hermetic seal 116 is arranged to seal the cavity 112 and prevent this gas from escaping. This is important for two reasons. Firstly, if gas escapes then the pressure is no longer known, and the device may need recalibrating or replacing. Secondly, in certain uses, e.g. in the cardiovascular system, escaping gas may be harmful, or even fatal, to the patient.

When sealed as described above, both components 102 of the assembly are contained within the hermetic seal 116, and are thus protected from the external environment. It will be noted that the design shown includes the via 114 connecting the top and bottom surfaces of the body 110 to one another. In order to maintain the hermetic seal, the via is also hermetically sealed, as described in more detail below in reference to FIGS. 4A and 4B. Equally, in some embodiments, no via is provided at all, and this is not an issue.

The assembly of components 102 are arranged to respond to electrical signals, and may be used for measuring various properties of their surrounding environment. For example, when implanted in a human or animal body, they may measure fluid pressure, fluid flow, local temperature, or other common measurements. The assembly 102 is at least partially enclosed between the body 110 and the membrane 100, providing protection from the external environment. Moreover, in some embodiments, one or more parts of the assembly 102 may be located on the outside of the device, in contact with the external environment, so that comparative measurements may be made with reference to components located between the body 110 and the membrane 100. Alternatively, certain measurement types, e.g. chemical composition of the surroundings, may require direct contact between the component and the environment.

When measuring fluid pressure, for example measuring intravascular pressure, the assembly 102 may measure this relative to a reference pressure in the cavity 112, for example by providing one or more pressure sensors as part of the assembly of components and comparing the external pressure to the pressure in the cavity. Alternatively, a pressure measurement may be made using one or more interdigitated transducers (IDTs), which form part of the assembly of components. These can be arranged so that the membrane 100 or the body 110 provides a substrate for the one or more IDTs. In particular, one or more of the IDTs may be arranged to detect a deflection of the membrane as part of sensing the intravascular pressure. A specific arrangement may be that a first IDT is located in a first region of the membrane which is arranged to deflect due to changes in intravascular pressure more than a second IDT located in a second region of the membrane. For example, the first IDT may be located in fluid communication the cavity 112, and may deflect into the cavity, compressing a gas in the cavity (wherein the amount of gas is already known). The second IDT may be located away from the cavity, and therefore is less able to deflect.

Similarly, while the cap 120 is shown separate from the body 110, when assembled, the cap 120 is joined, by joints 126 on its upper surface, to the bottom surface of the body 110 so that the channels 122, 124 are held against the bottom surface of the body 110. In some embodiments, the cap 120 is not included, and the device comprises only the body 110 and the membrane 100. While three channels 122a, 122b, 124 are shown, there may be more or fewer channels, depending on the specific requirements of the device. Each channel may not extend all the way across the cap, as shown, but instead may terminate part way across the cap 120. In addition, while the channels are shown as straight channels, they may be curved or bent, depending on the specific requirements.

The membrane 100, body 110 and cap 120 may be formed of the same material, for example to reduce strains due to differential thermal expansion during the assembly process. This may mean that the membrane and the body may comprise essentially the same material. Alternatively, the membrane and the body may each consist solely of the same material. Moreover, this material may be a piezoelectric material such as quartz, since piezoelectric materials may be used as part of a surface acoustic wave (SAW) device, in combination with an IDT. It may be particularly advantageous to align each IDT with the same crystal direction of the substrate on which the IDT is provided. That is to say that the angle between the interlaced digits of the IDT and a particular crystalline axis is the same for each IDT.

While each of the membrane 100, body 110 and cap 120 are shown as having approximately the same footprint (that is, having the same area in plan, as shown schematically in FIGS. 3A to 3C), this is not necessary, and one or other of these parts may extend beyond any of the others. For example, the cap 120 may extend beyond the base, resulting in one or more channels 122, 124 that are not completely covered by the body 110. Indeed, the channels 122, 124 may even be disposed on a surface other than a major surface of the cap 120.

The hermetic seal 116 may be formed in any suitable manner. In particular, a metal interlayer may be positioned between the body 110 and the membrane 100. The metal interlayer may form a diffusion bond such as a thermocompression bond, in which some of the metal interlayer diffuses into the crystal lattice of the body and the membrane, forming a hermetically sealed bond. Such a metal interlayer may be formed as a eutectic bond, in which an alloy, rather than an elemental metal, is used as the metallic interlayer. Specifically, the alloy is chosen to depress the melting point of the alloy, thus allowing a diffusion bond to be formed at a lower temperature. A lower temperature bonding process is desirable as it simplifies the construction of the device, as well as reducing strains on the device due to thermal expansion.

Alloys suitable for such bonding may include a base material and a dopant comprising, for example, a gold base material and a dopant. Base materials should have a good diffusivity in crystalline materials such as quartz and silicon. Gold is an example of such a base material. Suitable dopants contribute to the lowering of the melting temperature of the composition. Indium and tin are suitable examples of dopants for lowering the melting point of the eutectic composition. In particular, dopant levels of at least 15% by mass, at least 20% by mass, or even at least 25% by mass are suitable. Specifically, a doping level of 20% tin in gold, or a doping level of 27% indium in gold are suitable for the present application.

Figure 4A:
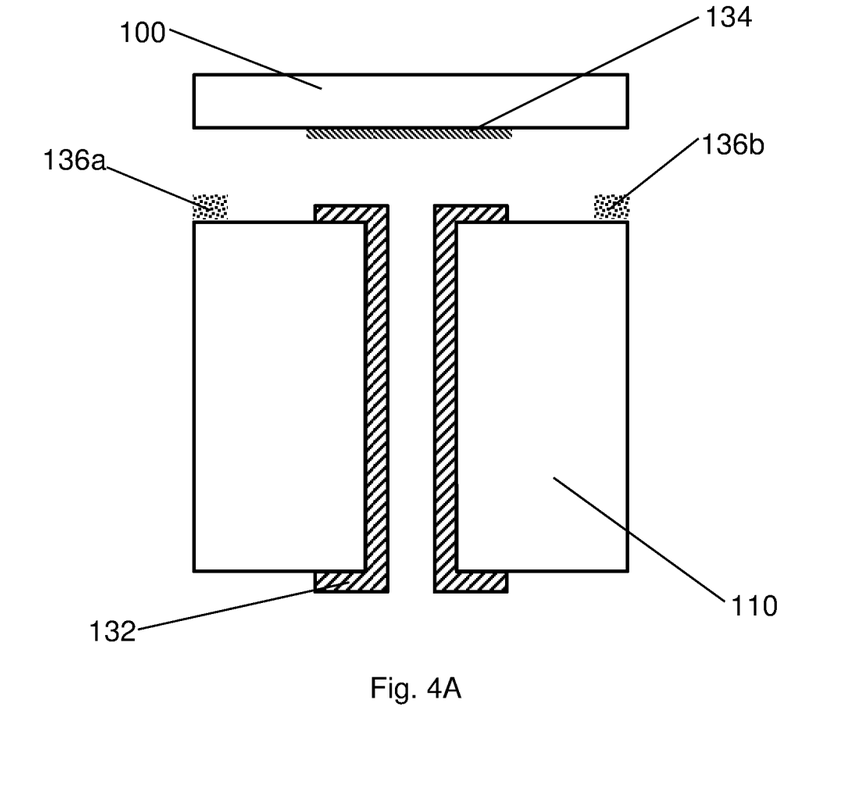
FIG. 4A shows an example of a via shown in FIGS. 1, 2 and 3B, showing the view in the direction of the arrows from section line 4-4 in FIG. 1.

Turning now to FIG. 4A, in which the via 114 is shown in more detail. As shown herein, the via 114 has a flanged tube1 running through it. The tube 132 fits closely to the inner walls of the via 114, and the flanges extend on to each of the top and bottom surfaces of the body 110, thus holding the tube 132 in place. Disposed on the membrane 100, directly above the via 114 (and also above the flanged tube 132) is a pad 134.

During assembly, as usual the hermetic seal 116 is formed to join the body 110 to the membrane 100, as described above. In addition, the flanges of the flanged tube 132 are pressed into contact with the pad 134, forming another hermetic seal. This seal ensures that the via 114 does not prevent the hermetic seal 116 from isolating parts of the device from the outside environment.

The flanged tube 132 may be formed of a conductive material to allow electrical signals to propagate into the sealed enclosure. In addition, the pad 134 may also be made from a conductive material to provide a path by which electrical signals may be sent to and received from the membrane 100. In addition, the flanged tube 132 and the pad 134 may form a eutectic bond in the manner described above in respect of the eutectic bond 116 which bonds the body 110 to the membrane 100. At the base of the body 110, the via 114 and flanged tube 132 may be arranged to align with the connection channel 124 in the cap 120, as described in more detail below. When there is a cap present, a pad may be positioned on the cap 120 instead of, or in addition to the cap 134 shown on the membrane 100 in FIG. 4A.

Figure 4B:
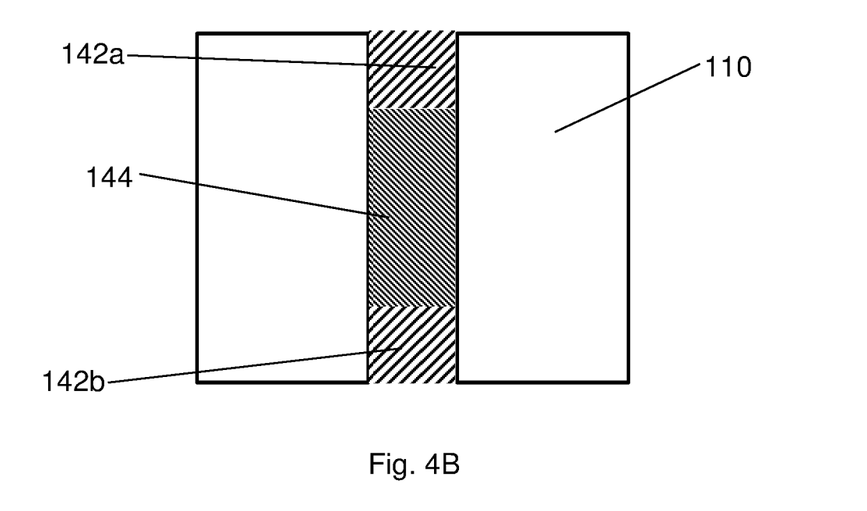
FIG. 4B shows another example of a via shown in FIGS. 1, 2 and 3B showing the view in the direction of the arrows from section line 4-4.

Turning now to FIG. 4B, another detail of a via 114 is shown. In this example, the bore of the via is filled with conductive materials. In this example, the parts of the via 114 closest to the top and bottom surfaces of the body 110 are filled with a capping material 142a, 142b, while the remainder of the via (the middle portion) is filled with a filling material 144. Both of the capping material and the filling material are electrically conductive, thus allowing electrical signals to propagate through the via 114. Since each of the capping and filling materials fill the via, however, the hermetic seal between the body and the membrane (not shown) is able to isolate parts of the device (e.g. the cavity 112) from the external environment.

The filling material may comprise copper. This is a suitable choice, as a filling material should be a good electrical conductor, but also relatively cheap. The capping material may comprise gold. A suitable capping material should be a good electrical conductor, but is also malleable. Malleability allows the capping material to deform when the via deforms (e.g. due to thermal expansion during the assembly of the device), thereby maintaining the seal.

While the via shown in FIG. 4B comprises two regions filled with capping material 142a, 142b, only a single such region need exist. Indeed, the entire via could be filled with capping material. Once again, the vial can be arranged so that the connection channel 124 in the cap 120 (not shown) aligns with the bottom end of the via 114, as described in more detail below.

In each of FIGS. 4A and 4B, the via may take any cross sectional shape, for example, while FIG. 3B shows a circular cross section, corresponding to a cylindrical bore, the vial could be any regular or irregular polygon, for example square or hexagonal. Similarly, while the axis of the cylinder is shown oriented perpendicularly to the top and bottom surfaces of the body 100, the via could traverse the body at an angle.

Figure 5:
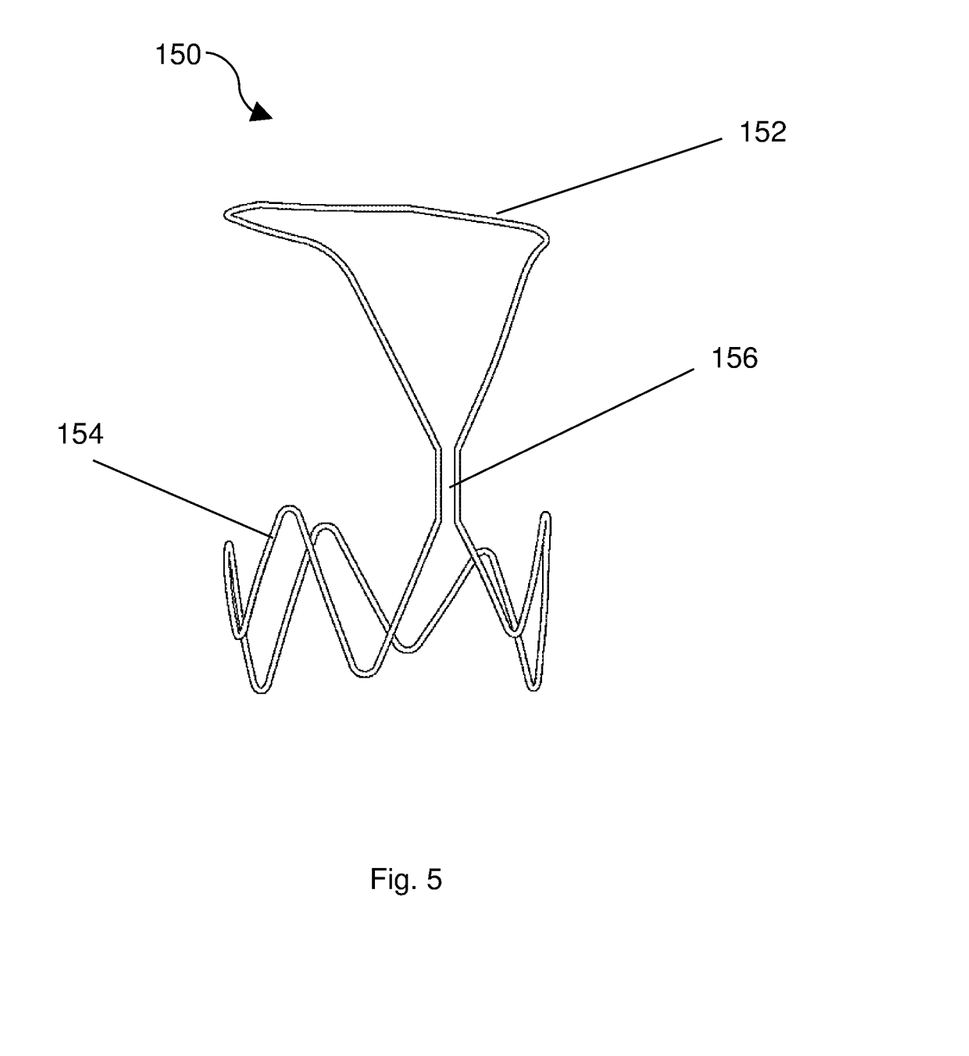
FIG. 5 shows an anchor for implanting an implantable device into a lumen of a body, for example a vein or artery.

Turning now to FIG. 5, there is shown an anchor 150 for supporting the device in a lumen of the human or animal body. In particular, the anchor 150 shown may be particularly suitable for supporting the device in a vascular lumen of the human or animal body. The anchor 150 comprises an upper portion 152, and lower portion 154 and a central portion 156. The upper 152 and lower 154 portions form loops, which are arranged to contact the walls of the lumen when the anchor is inserted into a lumen, while the central portion is adapted to support a device, as described below with reference to FIG. 6.

Figure 6:
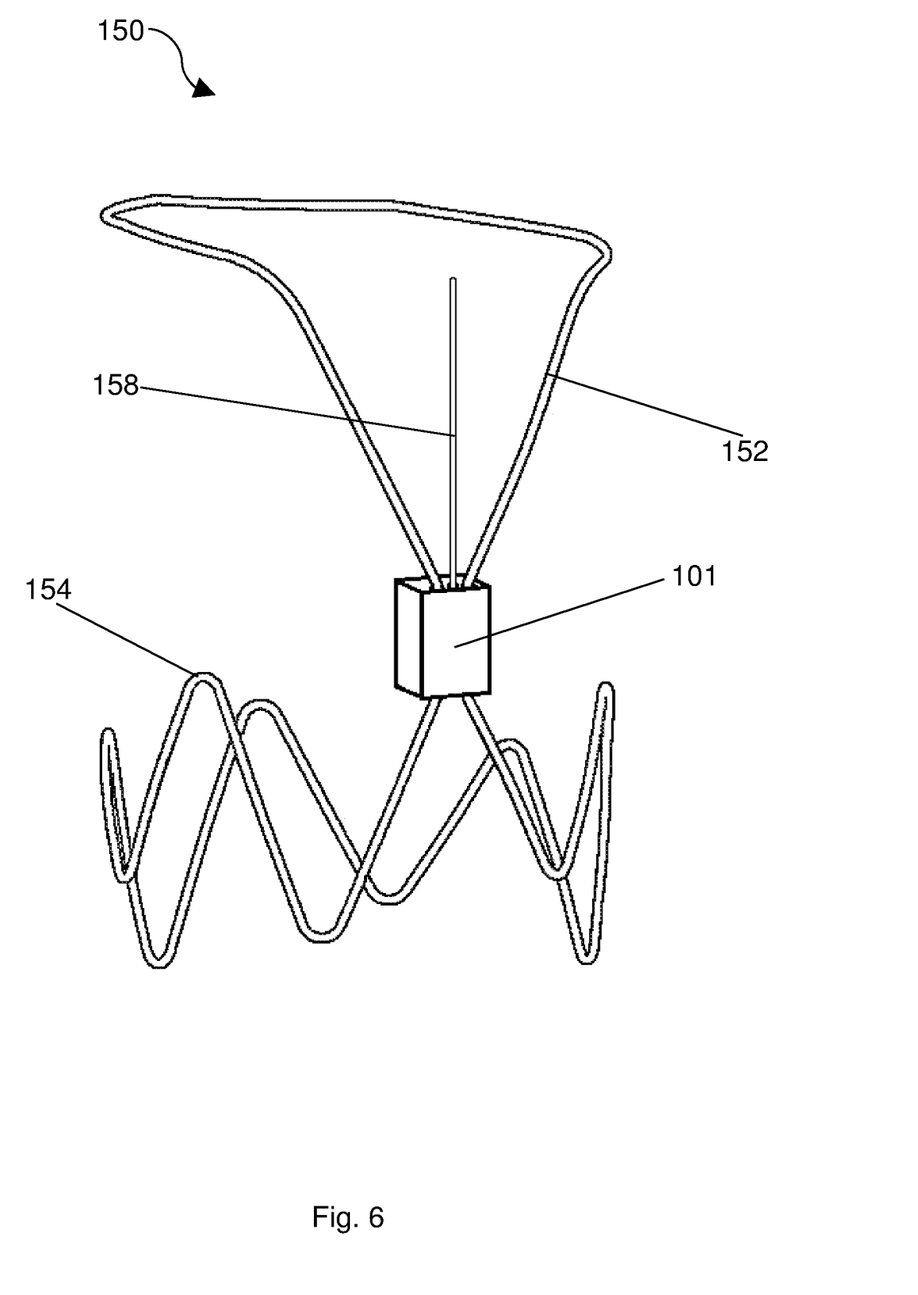
FIG. 6 shows an implantable device mounted on the anchor of FIG. 5.

Turning now to FIG. 6, the anchor of FIG. 5 is shown with a device 101 as described above mounted on the central portion 156. An antenna 158 is shown inserted into the connection channel 124 of the cap 120. The cap 120 is bonded to the body 110 so that the connection channel 124 is located against the base of the body 110. As described above, the via 114 may terminate in the connection channel 124. In this case, the via 114 (not shown in FIG. 6) provides a means by which the antenna can send and receive electrical signals into the hermetically sealed interior of the device. In this example, this allows the portions of the assembly of components 102b which are located adjacent to the cavity 112 to be in electrical contact with the antenna 158, while the cavity remains hermetically sealed from the external environment.

In addition, the frame of the central portion of the anchor 156 is shown inserted into the fixture channels 122 of the cap 120. Specifically, the central portion 158 of the anchor 150 comprises a pair of parallel struts, one of which is positioned in each of the fixture channels 122a and 122b. The cap 120 is bonded to the body 110 by bonds 126a and 126b, thereby holding the two struts against the base of the body 100 and fixing the device 101 to the anchor 150.

Although the device 101 is shown with both an anchor 150 and an antenna 158 fixed to the device 101 by the cap 120, it is envisaged that neither, or only one of these may be used, depending on the desired application. For example, the antenna may be entirely internal to the device, and thus would not require fixing to the body in this manner. Indeed, some designs may not even require an antenna at all. Similarly, no anchor may be required, depending on the intended application, and consequently no fixture channels need be provided. Depending on the design of the anchor, more or fewer fixture channels may be provided, for retaining struts of the anchor, or indeed for affixing other components to the device.

The cap 120 may be bonded to the body 110 by any suitable bonding means. For example, a room temperature bond may be desirable. This is because a room temperature bond reduces the potential for damage to the device when the device is heated. It may be desirable to prepare the bonding surfaces of the cap and the body using fast atomic bombardment prior to bonding, in order to improve bond quality.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Any apparatus feature as described herein may also be provided as a method feature, and vice versa. Furthermore, equivalents and modifications not described above may also be employed without departing from the scope of the invention, which is defined in the accompanying claims.

Throughout the description, relative terms like "above", "below", "to the left of", "to the right of" etc. have been used in conjunction with terms such as "upper", "lower" etc. to determine relative position. It is to be understood that these terms are used only for ease of understanding and do not imply any limitation on the orientation of any components relative to one another or in combination.

The invention claimed is:

1. An implantable intravascular device for deployment inside a human or animal, the apparatus comprising:
   a body of crystalline material and a membrane of crystalline material fixed to the body by a hermetic bond, wherein the hermetic bond comprises one of:
   (a) a metal interlayer between the membrane and the body; and
   (b) a room temperature bond;
   an assembly of components carried on said crystalline material and arranged for responding to electrical signals;
   wherein the assembly of components comprises:
   at least one InterDigitated Transducer (IDT);
   wherein the at least one IDT comprises:
   a first IDT disposed on the membrane to sense intravascular pressure based on deflection of the membrane;

the membrane provides a substrate for the at least one IDT;

wherein the body and the membrane at least partially encapsulate the assembly;

wherein the hermetic bond comprises a eutectic bond; and wherein the eutectic bond comprises gold, or gold comprising a dopant material which lowers the bonding temperature such as indium or tin.

2. The apparatus of claim 1 wherein the metal interlayer forms a diffusion bond such as a thermo-compression bond.

3. The apparatus of claim 1 wherein the body comprises a cavity and the hermetic bond seals the cavity to provide a sealed enclosure at a reference pressure.

4. The apparatus of claim 3 wherein the assembly is arranged to provide a pressure sensor for sensing intravascular pressure as compared to said reference pressure.

5. The apparatus of claim 1 wherein the dopant comprises at least 15% by mass of the bond, for example at least 20%, for example at least 25%, for example preferably wherein the dopant is 20% by mass of the bond if the dopant is Sn, and preferably wherein the dopant is 27% of the bond if the dopant is In.

6. The apparatus of claim 1 wherein the room temperature bond is formed by Fast Atomic Bombardment (FAB).

7. The apparatus of claim 1 wherein the at least one IDT comprises a second IDT disposed on a region of the crystalline material arranged to be deflected less by changes in intravascular pressure than the region which carries the first IDT.

8. An implantable intravascular device for deployment inside a human or animal, the apparatus comprising:

a body of crystalline material and a membrane of crystalline material fixed to the body by a hermetic bond, wherein the hermetic bond comprises one of:

(a) a metal interlayer between the membrane and the body; and (b) a room temperature bond;

an assembly of components carried on said crystalline material and arranged for responding to electrical signals;

wherein the assembly of components comprises:

at least one InterDigitated Transducer (IDT);

wherein the at least one IDT comprises:

a first IDT disposed on the membrane to sense intravascular pressure based on deflection of the membrane;

the membrane provides a substrate for the at least one IDT;

wherein the body and the membrane at least partially encapsulate the assembly; and wherein at least one channel is provided by at least one trench disposed in at least one of a cap and the body and at least partially covered by the respective other one of the cap and the body.

9. The apparatus of claim 8 wherein the at least one channel comprises a connection channel for securing an antenna to the apparatus.

10. The apparatus of claim 8 wherein the at least one channel comprises a fixture channel for fixing the apparatus to a strut of an anchor for supporting the apparatus inside the human or animal body.

11. The apparatus of claim 8 wherein the at least one channel comprises a fixture channel for fixing the apparatus to a strut of an anchor for anchoring the apparatus to a structure inside a human or animal.

* * * * *